US00PP15470P2

(12) United States Plant Patent
Rigney

(10) Patent No.: US PP15,470 P2
(45) Date of Patent: Jan. 4, 2005

(54) ***AGAPANTHUS* PLANT NAMED 'SNOW PIXIE'**

(50) Latin Name: *Agapanthus×hybrid*
Varietal Denomination: Snow Pixie

(76) Inventor: Ken Rigney, 137B King Georges Ave., Regents Park, Southampton SO15 4LE (GB)

( * ) Notice: Subject to any disclaimer, the term of this patent is extended or adjusted under 35 U.S.C. 154(b) by 10 days.

(21) Appl. No.: 10/456,155

(22) Filed: Jun. 6, 2003

(51) Int. Cl.[7] ..... A01H 5/00
(52) U.S. Cl. ..... Plt./263
(58) Field of Search ..... Plt./263

*Primary Examiner*—Anne Marie Grunberg
*Assistant Examiner*—June Hwu

(57) ABSTRACT

A new cultivar of *Agapanthus* named 'Snow Pixie' that is characterized by a compact dwarf habit, green sword-shaped leaves and a floriferous display of white flowers. In combination these traits set 'Snow Pixie' apart from all other existing varieties of *Agapanthus* known to the inventor.

2 Drawing Sheets

Genus: *Agapanthus.*
Species: ×*hybrida.*
Denomination: Snow Pixie.

BACKGROUND OF THE INVENTION

The present invention relates to a new and distinct cultivar of Lily-of-the-Nile grown for use as an ornamental plant for the landscape. The new cultivar is known botanically as *Agapanthus* and will hereinafter be referred to as 'Snow Pixie'.

The inventor collected seed from a unique *Agapanthus* in a cultivated area of Durban, South Africa. In 1990 the seeds were sown in a cultivated area of West Sussex, United Kingdom. The resulting seedlings were grown out and observed for a number of years. In 1996 'Snow Pixie' was selected by the inventor based on the criteria of habit and number of flowers. The selected seedling also proved hardy, remaining evergreen when the temperature dropped to −9.5° Centigrade.

'Snow Pixie' is a chance hybrid plant that is floriferous and exhibits a compact dwarf habit. The parents of 'Snow Pixie' are *Agapanthus* hybrids. The female parent is an unnamed *Agapanthus* hybrid (unpatented) and the male parent is an unidentified *Agapanthus* hybrid (unpatented).

When compared with the population of plants from which seed was collected, 'Snow Pixie' was observed to be consistently shorter in overall height, typically around 54 cm including the flower scapes. The presumed parental material achieves an overall height in the range 75 cm to 90 cm. The existing commercial variety *Agapanthus* 'Snowstorm', U.S. Plant Pat. No. 12,554 achieves height in the range 70 cm to 75 cm.

When compared with plants of like age (whether first year flowering or subsequent year of flowering) taken from the parental seedling population, 'Snow Pixie' has been observed to carry far more (up to three times as many) flower scapes than a typical grown-on seedling taken from the original population.

'Snow Pixie' was first asexually propagated in 1996, in a cultivated area of West Sussex, United Kingdom, under the direct supervision of the inventor. The method used for asexual propagation was tissue culture. Since that time under careful observation, successive generations have been determined stable and true to type. Asexual propagation can also be accomplished by division.

SUMMARY OF THE INVENTION

The following traits have been repeatedly observed and represent the distinguishing characteristics of the new *Agapanthus* variety known as 'Snow Pixie'. These traits in combination distinguish 'Snow Pixie' from all other existing varieties of *Agapanthus* known to the inventor. 'Snow Pixie' has not been tested under all possible conditions and phenotypic differences may be observed with variations in environmental, climatic, and cultural conditions, however, without any variance in genotype.

1. *Agapanthus* 'Snow Pixie' is a chance hybrid.
2. *Agapanthus* 'Snow Pixie' exhibits white flowers.
2. *Agapanthus* 'Snow Pixie' exhibits a compact dwarf habit.
3. *Agapanthus* 'Snow Pixie' is floriferous, exhibiting 50–54 flowering scapes at maturity and approximately 24–30 florets per flower-head.
4. *Agapanthus* 'Snow Pixie' blooms in late spring and early summer.
5. *Agapanthus* 'Snow Pixie' is 54 cm. in height and 36–40 cm. in width.
6. *Agapanthus* 'Snow Pixie' exhibits medium-green sword-shaped leaves.
7. *Agapanthus* 'Snow Pixie' is a perennial ornamental plant for use in container and landscape.
9. *Agapanthus* 'Snow Pixie' is hardy to −9.5° Centigrade.

BRIEF DESCRIPTION OF THE DRAWINGS

The accompanying color drawings illustrate the overall appearance of the new variety 'Snow Pixie' showing the colors as true as it is reasonably possible to obtain in colored reproductions of this type. The plants in the drawings are 18-months-old and grown out-of-doors in Santa Barbara, Calif. Colors in the drawings may differ from the color values cited in the detailed botanical description, which accurately describe the actual colors of the new variety 'Snow Pixie'.

The drawing on sheet 1 illustrates the entire plant from a side perspective.

The drawing on sheet 2 is a close-up view of the flowers.

Drawings were made using conventional photographic techniques and although flower and foliage colors may appear different from actual colors due to light reflectance, they are as accurate as possible by conventional photography.

BOTANICAL DESCRIPTION OF THE PLANT

The following is a detailed description of the new *Agapanthus* cultivar named 'Snow Pixie'. Datum was compiled in Arroyo Grande, Calif. from a 36-month-old plant grown out-of-doors in a 4-liter container. Color determinations are in accordance with The 2001 Royal Horticultural Society Colour Chart except where general color terms of ordinary dictionary significance are used. The growing requirements are similar to the species.

Botanical classification: *Agapanthus* 'Snow Pixie'.
Species: ×*hybrida*.
Common name: Lily-of-the-Nile.
Use: Ornamental suitable as a container plant or massed in the landscape.
Type: Perennial herb.
Parentage: 'Snow Pixie' is a chance hybrid that resulted from the open pollination of the following parent plants:
*Female parent plant.*—Unnamed *Agapanthus* hybrid.
*Male parent plant.*—Unidentified *Agapanthus* hybrid.
Growth rate: Vigorous.
Growth habit: Compact dwarf.
Form: Clumping.
Plant height: 54 cm. in height.
Plant width: 36–40 cm. in width.
Plant shape: Stout and fountain-shaped.
Hardiness: Hardy to −9.5° Centigrade.
Propagation: Asexual propagation can be accomplished using tissue culture and division.
Root system: Thick and fleshy.
Cultural requirements: Full sun, well-drained soil and regular water.
Cropping time: Approximately 8–12 months is needed to produce a commercial 1-liter container plant from division.
Seasonal interest: White flowers.
Blooming season: Late spring and early summer.
Diseases and pests: No other diseases or pests known to the inventor.
Foliage:
*Type.*—Evergreen.
*Leaf shape.*—Ensiform.
*Leaf form.*—Arching.
*Branching habit.*—Basal.
*Leaf apex.*—Acute.
*Leaf base.*—Truncate.
*Leaf division.*—Simple.
*Leaf attachment.*—Sheathing.
*Leaf margins.*—Entire and slightly involute.
*Leaf color* (*adaxial surface*).—138A.
*Leaf color* (*abaxial surface*).—138B.
*Leaf surface* (*adaxial surface*).—Matte to glaucous.
*Leaf surface* (*abaxial surface*).—Matte to glaucous.
*Pubescence.*—None.
*Venation pattern.*—Parallel.
*Color of veins* (*abaxial and adaxial surfaces*).—138D.
*Leaf length.*—23 cm. in length.
*Leaf width.*—1.5 cm. in width.
*Leaf fragrance.*—None.
*Leaf texture.*—Sub-coriaceous.
Flower:
*Flowering months.*—April, May, and June.
*Inflorescence type.*—Terminal umbel subtended by 2 papery valves.
*Valve dimensions.*—1 cm. in width and 2.5 cm. in length.
*Valve color.*—159C and 174A are both individually present on an individual valve.
*Dimensions of inflorescence.*—8 cm. in length and 12 cm. in width.
*Number of flowers per umbel.*—24–30 flowers per umbel.
*Persistent or self-cleaning.*—Self-cleaning.
*Lastingness of an individual umbel.*—3 weeks, when defined as the elapsed time between the opening of the first individual flower and the opening of the last individual flower.
*Flower aspect.*—Facing upward and outward.
*Number of scapes.*—Approximately 50–54 at maturity.
*Dimensions of scape.*—48–50 cm. in length and 0.50 mm. in width.
*Scape color.*—144A.
*Scape texture.*—Smooth.
*Shape of scape.*—Cylindrical and slightly tortuous.
*Scape surface.*—Glaucous.
*Pedicel color.*—144A.
*Pedicel dimensions.*—1.5 cm. in length and 2 mm. in diameter.
*Flower shape.*—Funnel.
*Lastingness of an individual flower.*—5 days to 7 days.
*Flower dimensions.*—Diameter at apex 2.5 cm–3.0 cm; Length 3.5 cm.
*Petals.*—Apetalous.
*Number of tepals.*—Six in number.
*Fused or unfused.*—Basally fused.
*Tepal shape.*—Spatulate.
*Tepal margin.*—Minutely fringed.
*Tepal surface* (*adaxial surface*).—Furrowed.
*Tepal surface* (*abaxial surface*).—Glabrous.
*Tepal color.*—155D.
*Tepal dimensions.*—3.50 cm. in length and 1 cm. in width.
*Tepal apex.*—Apiculate, slightly reflexed.
*Bud shape.*—Obelliptic.
*Bud dimensions.*—1 cm. in diameter and 2 cm. in length.
*Color of bud.*—155B.
*Bud surface.*—Glabrous.
*Flower fragrance.*—None.
Reproductive organs.
*Stamens.*—6 in number adnate to hypanthium.
*Stamen color.*—155B.
*Stamen dimensions.*—3 cm. in length and 0.50 mm. in width.
*Anther color.*—15A.
*Anther shape.*—Longitudinal.
*Anther dimensions.*—2 mm. in length and 1 mm. in width.
*Pollen color.*—15A.
*Amount of pollen.*—Moderate amount.
*Pistil.*—One present.
*Pistil shape.*—Filament.

*Pistil color.*—155B.
*Pistil dimensions.*—1 mm. in width and 2 cm. in length.
*Ovary color.*—10D.
*Ovary shape.*—Elongated oval.
*Ovary dimensions.*—0.75 cm. in length and 3 mm. in width.
*Ovary position.*—Superior.

Seed:

*Fruit.*—Capsule.
*Fruit dimensions.*—1.75 cm. in length and 0.75 cm. in width.
*Fruit color.*—159B.
*Fruit surface.*—Glossy.
*Number of seeds.*—Four in number.
*Seed color.*—202A.
*Seed surface.*—Waxy coating.
*Seed dimensions.*—6 mm. in length and 5 mm. in width.

It is claimed:

1. A new and distinct variety of *Agapanthus* plant named 'Snow Pixie' as described and illustrated.

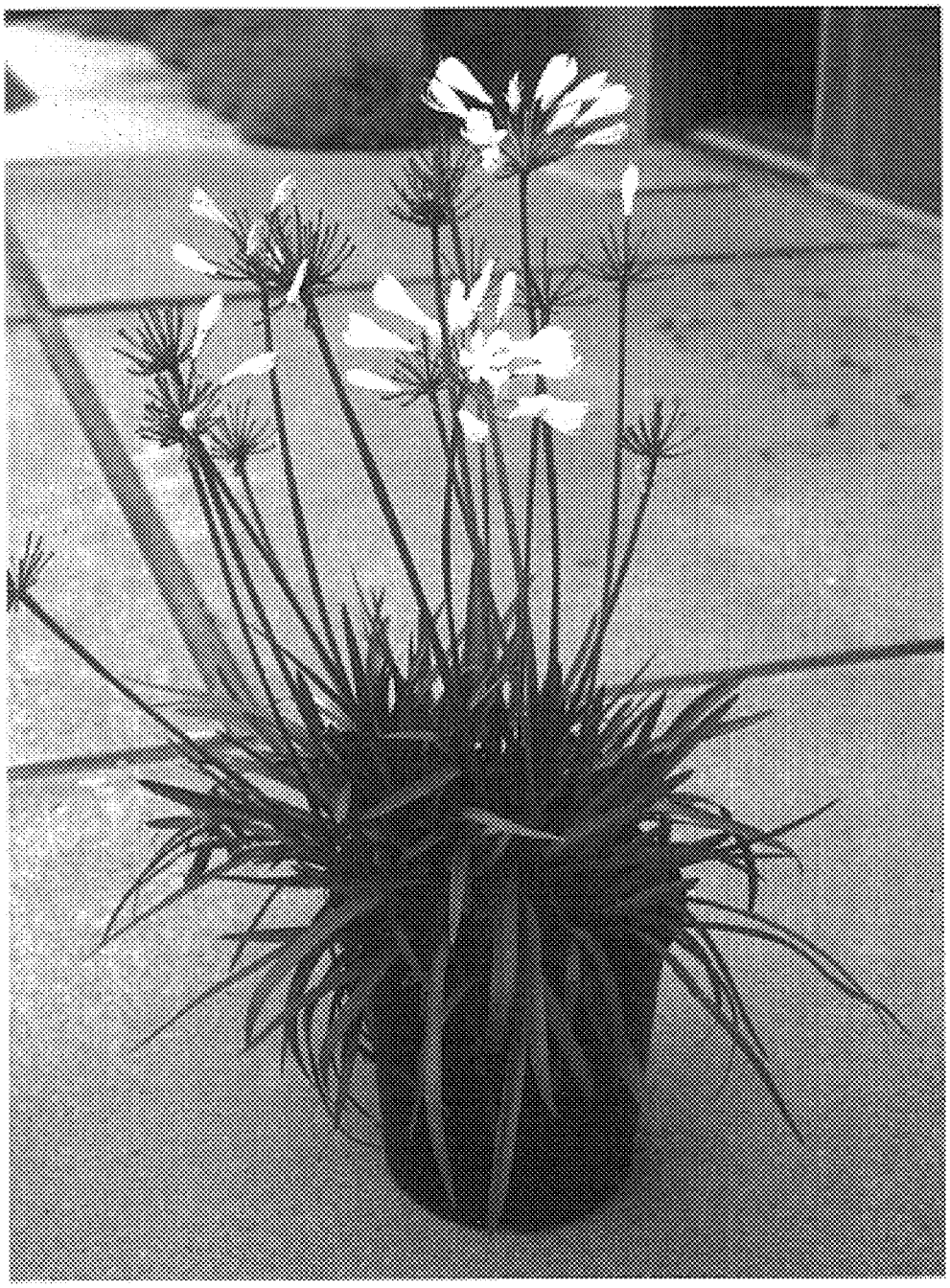

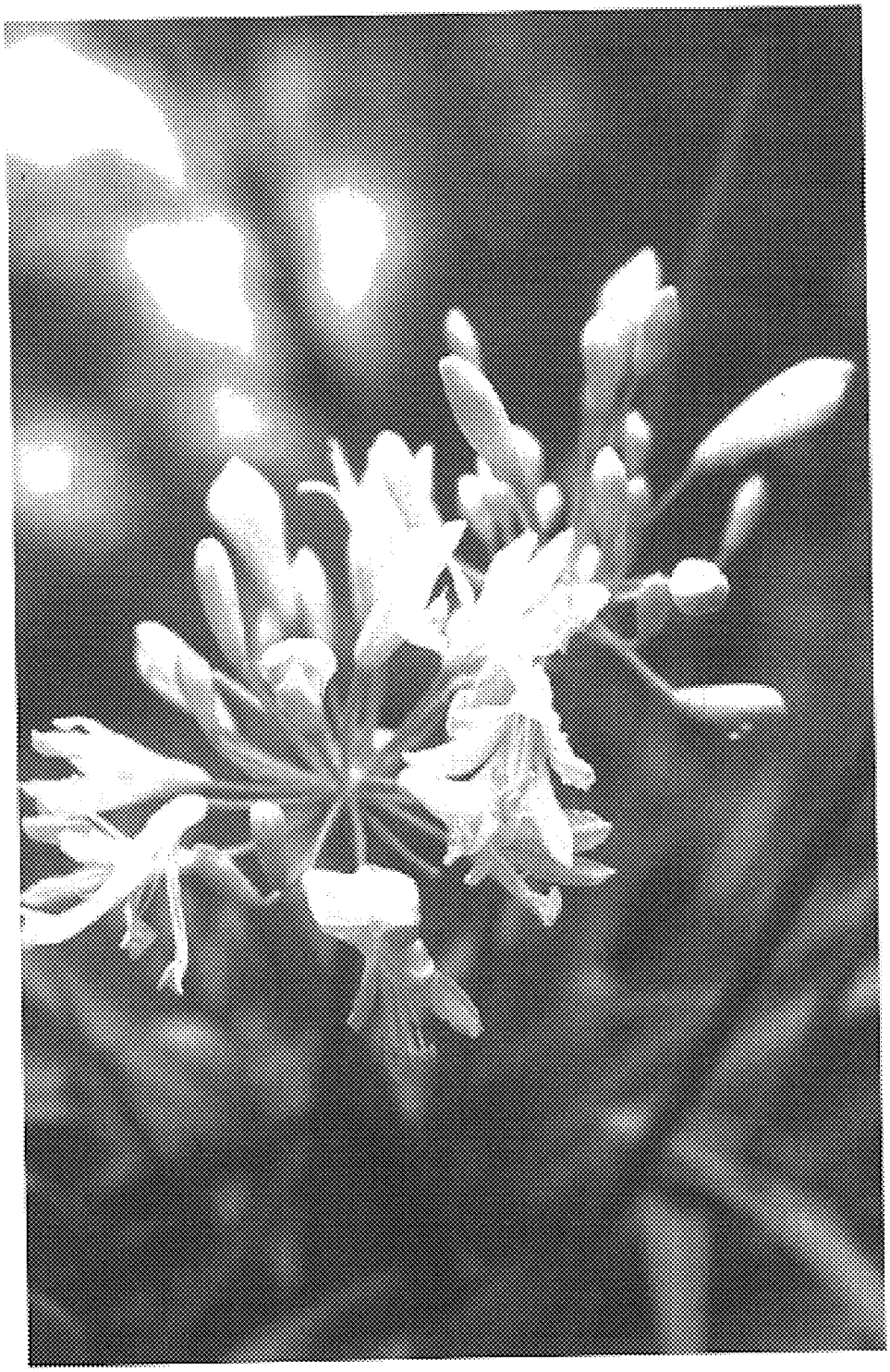

* * * * *